United States Patent [19]
Lodaya et al.

[11] Patent Number: 6,114,554
[45] Date of Patent: Sep. 5, 2000

[54] PREPARATION OF QUINONEDIIMINES FROM PHENYLENEDIAMINES USING A HYPOCHLORITE AS AN OXIDATION AGENT

[75] Inventors: Jayant Shivji Lodaya, Akron; Raymond Anton Lohr, Jr., Avon; Donald Lee Fields, Jr., Copley, all of Ohio

[73] Assignee: Flexsys America L.P., Akron, Ohio

[21] Appl. No.: 09/089,551

[22] Filed: Jun. 3, 1998

Related U.S. Application Data

[60] Provisional application No. 60/063,764, Oct. 29, 1997.

[51] Int. Cl.$^7$ .................................................. C07C 50/04
[52] U.S. Cl. ......................... 552/301; 546/329; 546/561; 552/302; 562/440; 564/191; 564/248; 564/277
[58] Field of Search ..................................... 552/301, 302; 564/248, 277, 191; 562/440; 546/329, 561

[56] References Cited

U.S. PATENT DOCUMENTS

| | | | |
|---|---|---|---|
| 2,118,826 | 5/1938 | Semon | 260/56 |
| 4,264,776 | 4/1981 | Hershman et al. | 564/384 |
| 4,624,937 | 11/1986 | Chou | 502/180 |
| 4,696,772 | 9/1987 | Chou | 260/502.5 |
| 5,091,545 | 2/1992 | Parker | 552/302 |
| 5,118,807 | 6/1992 | Wheeler | 544/197 |
| 5,189,218 | 2/1993 | Desmurs et al. | 564/272 |
| 5,208,280 | 5/1993 | Wheeler | 524/100 |
| 5,371,289 | 12/1994 | Cottman et al. | 564/396 |
| 5,672,725 | 9/1997 | Polis | 552/293 |

FOREIGN PATENT DOCUMENTS

| | | |
|---|---|---|
| 162035 | 11/1985 | European Pat. Off. . |
| 0 708 080 | 4/1996 | European Pat. Off. . |
| 708080 | 4/1996 | European Pat. Off. . |
| 708081 | 4/1996 | European Pat. Off. . |
| 2659651 | 3/1991 | France . |
| 2659650 | 9/1991 | France . |
| 157 288 | 12/1904 | Germany . |

OTHER PUBLICATIONS

Corbett, J. F., Chem Abst. 78:83602, 1973.
Boozer et al, "Air Oxidation of Hydrocarbons . . .", 77, J. Am. Chem. Soc., 3233, 1955.
*International Search Report*, dated Jun. 16, 1999 (PCT/IB99/00597).
R. Lantz, et al: Bulletin De La Societe Chimique De France, vol. 33, No. 4, May 22, 1925, pp. 890–901 and English Translation.

*Primary Examiner*—Peter O'Sullivan
*Attorney, Agent, or Firm*—Louis A. Morris

[57] ABSTRACT

A phenylenediamine compound can be converted, with high selectivity, into its corresponding quinonediimine by reacting the phenylenediamine with a hypochlorite oxidation reactant.

31 Claims, No Drawings

PREPARATION OF QUINONEDIIMINES FROM PHENYLENEDIAMINES USING A HYPOCHLORITE AS AN OXIDATION AGENT

This application claims priority to the filing date of U.S. Provisional Application No. 06/063,764, filed Oct. 29, 1997.

FIELD OF THE INVENTION

This invention relates to a process for preparing quinonediimines from their corresponding phenylenediamines using a hypochlorite as an oxidation agent.

BACKGROUND OF THE INVENTION

The class of cyclic enones is well known in organic chemistry. Best known examples of cyclic enones are quinones such as, for example, the benzoquinones, naphthoquinones, anthraquinones, phenanthraquinones, and the like. 1,4-Benzoquinone is commonly referred to as quinone. Quinones are generally brightly colored compounds and have versatile applications in chemical synthesis, biological uses, as redox materials, as well as in industry. There are several review articles on the chemistry and applications of quinones including, for example, *Kirk-Othmer Encyclopedia of Chemical Technology*, Third ed., Vol. 19, pages 572–605, John Wiley & Sons, New York, 1982.

The synthesis of quinones is well documented. See, for example, J. Cason, *Synthesis of Benzoquinones by Oxidation, in Organic Synthesis*, Vol. IV, page 305, John Wiley & Sons, New York (1948). Quinones generally are prepared by oxidizing the appropriately disubstituted aromatic hydrocarbon derivatives, the substituents being hydroxyl or amino groups in the ortho or para positions. 1,4-Benzoquinone, for example, can be made from the oxidation of hydroquinone, p-aminophenol or p-phenylenediamine, or from quinic acid. The reagents generally used for the oxidation are dichromate/sulfuric acid mixture, ferric chloride, silver (II) oxide or ceric ammonium nitrate. In these cases, oxidation of the aminoaromatic compound is accompanied by hydrolysis to the corresponding quinone. Some processes may take several hours for completion of the reaction.

Thus, some of the prior art processes utilize a catalytic agent to achieve an acceptable reaction rate while other processes proceed without catalysts. The process according to the present invention utilizes a hypochlorite reagent which provides extremely high conversion, high selectivity, and fast reaction rates to prepare the quinonediimine.

A prior art process which utilizes a catalyst in the preparation of a quinoneimine compound is disclosed by Desmurs, et al. in U.S. Pat. No. 5,189,218. The process of Desmurs, et al., which converts N-(4-hydroxyphenyl)aniline into N-phenylbenzoquinone-imine, utilizes a manganese, copper, cobalt, and/or nickel compound as a catalyst in an oxidation type reaction.

The above process of Desmurs, et al., which uses a metal catalytic component, along with any other processes which utilize a metal catalyst, have several drawbacks. Not only are the metal catalysts relatively expensive, they raise important environmental concerns. For example, effluent streams and products can be contaminated by the metals. Further, recovery of the catalyst for reuse can be prohibitively expensive.

Other processes are known which use oxidizing agents to convert phenylenediamines into their corresponding quinonediimines. For example, EP 708,081 (Bernhardt et al), which describes the conversion of phenylenediamines to phenylenediimines by oxidation of the diamine in an alkali/alcoholic solution, gives a general description of such processes in its background. The EP '081 process suffers from various disadvantages including long reaction times and low yields. Additional oxidation conversion processes are described by Wheeler in U.S. Pat. No. 5,118,807 and by Haas et al, in EP 708,080. However, the use of a hypochlorite as an oxidizing agent in the conversion of diamino compounds to give highly selective yields of diimino compounds has not heretofore been suggested.

As such, the current invention is based on the problem of providing a simple and economic process for the preparation of N,N'-disubstituted quinonediimines in high yields and with high purity.

SUMMARY OF THE INVENTION

It has been discovered that phenylenediamine compounds can be converted with extremely high selectivity into the corresponding quinonediimine by reaction of the diamine with a hypochlorite oxidant. Conditions are revealed in which nearly quantitative yields have been obtained.

In contrast to prior art, an advantage of the present invention is that the conversion of phenylenediamine to the corresponding quinonediimine is nearly quantitative. Thus, very little waste material remains upon completion of the reaction.

Another advantage comes from the use of the hypochlorite oxidizing agent. The hypochlorite oxidizing agent avoids the drawbacks associated with metal catalysts which include high cost, product contamination and environmental waste concerns.

An addtional advantage is that the hypochlorite oxidizing agents, as set forth herein, provide an extremely high conversion, high selectivity and faster more complete reaction compared to prior art processes.

Still further advantages of the present invention will become apparent to those skilled in the art upon reading and understanding the following detailed description of the preferred embodiments.

DETAILED DESCRIPTION OF THE INVENTION

The object of the present invention is to provide an effective process for converting phenylenediamines into their corresponding quinonediimines (QDI's).

In accordance with the object of the invention, a phenylenediamine (ortho or para) according to Formula I:

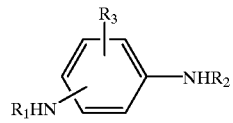

Formula I wherein $R_1$, $R_2$ and $R_3$ are the same or different radicals selected from hydrogen, hydroxyl, halogen, alkyl, alkoxy, aryl, aralkyl, alkaryl, cycloalkyl, heterocycle, acyl, aroyl, carbamyl, carboxylic acids, esters, ethers, ketones, alcohols, thiols, alkylthiols, and cyano, is reacted with a hypochlorite oxidizing agent.

The reaction produces a corresponding quinonediimine according to Formula IIa or IIb:

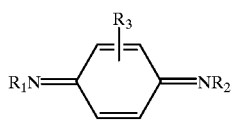

Formula IIa

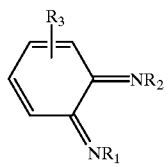

Formula IIb wherein $R_1$, $R_2$ and $R_3$ are the same as in the compound according to Formula I.

The reaction is represented as follows:

Reaction Scheme 1

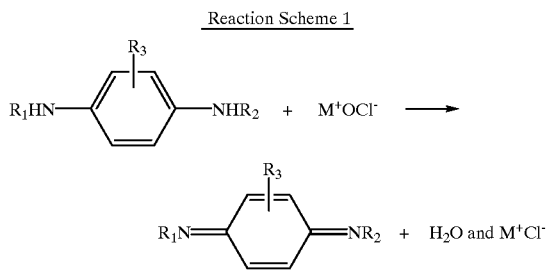

Examples of satisfactory radicals for $R_1$, $R_2$ and $R_3$ are linear or branched alkyls such as methyl, ethyl, propyl, butyl, pentyl, hexyl, heptyl, octyl, nonyl, decyl, dodecyl, and the like; aryls such as phenyl, naphthyl, anthracyl, tolyl, ethylphenyl, 1-ethyl-3-methylpentyl, 1-methylheptyl, and the like; cycloalkyls such as cyclobutyl, cyclopentyl, cyclohexyl, cyclooctyl, and the like. Other examples include allyl and isobutenyl; 1,3,5-sym-triazinyl, 2-benzothiazolyl, 2-benzimidazolyl, 2-benzoxazolyl, 2-pyridyl, 2-pyrimidinyl, 2,5-thiadiazolyl, 2-pyrazinyl, adipyl, glutaryl, succinyl, malonyl, acetyl, acrylyl, methacrylyl, caproyl, 3-mercaptopropionyl, benzoyl, phthaloyl, terephthaloyl, aminocarbonyl, carbethoxy, carbonyl, formyl, and the like. These are merely exemplary radicals and are in no way intended to limit the scope of the invention.

Hypochlorite agents include but are not limited to metal salts of hypochlorite, chlorate, perchlorate as well as organic hypochlorites such as t-butyl hypochlorite. In reaction scheme 1, as set forth above, M is selected from various metals such as sodium (Na), potassium (K) , and calcium (Ca) , or various organic groups such as alkyl, aryl and the like. The hypochlorite may be present in amounts ranging from 0.1 to 100 preferably 0.3 to 5 equivalents per equivalent of phenylenediamine. Using less than one equivalent of hypochlorite per equivalent of phenylenediamine allows one to produce blends of quinonediimine and unreacted phenylenediamine. When using more than one equivalent of hypochlorite, it is acceptable to recycle the unreacted hypohlorite stream.

It is additionally contemplated that sodium hypochlorite can be made in situ by passing chlorine through sodium hydroxide solution. For example, one can have a reactant mixture of N-1,3-dimethylbutyl-N'-phenyl-p-phenylenediamine (Santoflex® 6PPD) and sodium hydroxide and then add chlorine gas to the reactor in known amounts and make sodium hypochlorite in situ. This would, in turn, react with Santoflex® 6PPD to give 6QDI.

The reaction, according to the present invention, may take place in a solvent system. Various polar and non-polar solvents may be used in the oxidation reaction including various hydrocarbon based solvents and water. Organic solvents useable in the process of the present invention include, but are not limited to, alcohols such as methanol, ethanol, propanol, isopropanol, methyl isobutyl carbinol, ethylene glycol; ketones such as acetone, cyclohexanone, 4-methyl-2-pentanone (methyl isobutyl ketone), 5-methyl-2-hexanone, methyl ethyl ketone; aliphatic and aromatic hydrocarbons as such as hexanes, heptanes, toluene, xylenes; nitrites such as acetonitrile; halogenated solvents such as chloroform, dichloromethane, carbon tetrachloride; water soluable solvents such as dimethyl sulphoxide, N-methyl-2-pyrrolidone, sulfolane, dimethylformamide; esters such as ethyl acetate; ethers such as 1,4-dioxan and mixtures thereof. Water may also be used in the solvent systems alone or as a mixture with the organic solvent. The initial phenylenediamine concentration may range in amounts of from 1% to 100% w/v. Polar solvents may be used alone or in admixture with non-polar solvents to increase the rate of the reaction.

The present reaction may also take place in a neat system, without any solvent added. In a neat system, the phenylenediamine starting material is heated to a molten state, the hypochlorite is added and the mixture is stirred until completion of the reaction. The use of the neat system avoids the handling and flammability hazards associated with the use of solvents, especially the flammability hazards present when a solvent is used in an oxidation reaction.

The present reaction may take place at temperatures from −200° C. to 150° C., preferably from 0° C. to 100° C., depending on the solvent.

With water immiscible solvents it is advantageous to utilize a phase transfer catalyst to accelerate the rate of reaction in the process of the present invention. Phase transfer catalysts useable in the present invention include, but are not limited to, quaternary ammonium salts, such as tetramethyl ammonium hydroxide, tetra alkyl ammonium halides, tetra-N-butyl ammonium bromide, tetra-N-butyl ammonium chloride, benzyltriethyl ammonium chloride; phosphonium salts such as bis[tris(dimethylamino)phosphine]iminium chloride; crown ethers and polyethylene glycols.

A phase transfer catalyst can be added directly to the reaction mixture or it can be dissolved in one of the reagents such as sodium hypochlorite or Santoflex® 6PPD. The phase transfer catalyst may also be dissolved in a solvent used in the process or in water before addition to the reaction mass.

Another means by which the rate of recation may be increased is through increasing the stirring or mixing rate in the reaction. By increasing the stirring or mixing, the reaction rate may be effectively adjusted to proceed at a faster pace when necessary.

Agents such as sodium sulfite or other neutralizing agents can be added before the workup of the reaction mixture to neutralize any excess of sodium hypochlorite if present in the mixture.

The present invention can be more clearly illustrated by the following examples.

EXAMPLE 1

A mixture of N-1,3-dimethylbutyl-N'-phenyl-p-phenylenediamine (Santoflex® 6PPD, 60 g., 0.224 moles) and acetonitrile (250 mL) was stirred at room temperature. To this mixture was then added sodium hypochlorite (148 g., conc.=approx 11.2%, 0.23 moles). The mixture was stirred at room temperature for 1.5 hr. and then analyzed by HPLC for the consumption of starting material. Analysis indicated disappearance of Santoflex® 6PPD and formation of the corresponding quinonediimine. A variety of isolation techniques can be used to isolate the product. The technique used consisted of concentration of the reaction mass to remove acetonitrile followed by treatment with a hydrocarbon (for example Toluene 300 mL) and water, followed by layer separation and concentration of the hydrocarbon layer leading to a dark colored liquid. The product was identified to be the corresponding N-1,3-dimethylbutyl-N'-phenyl-quinonediimine (6QDI). The 6QDI was isolated in almost quantitative yields.

EXAMPLE 2

A mixture of N-1,3-dimethylbutyl-N'-phenyl-p-phenylenediamine (Santoflex 6PPD, 5 g., 0.019 moles) and methanol (200 mL) was stirred and cooled to −70° C. To this mixture was then added sodium hypochlorite (12 g., conc.= approx. 11.7%, 0.020 moles). The mixture was stirred at −70° C. and analyzed by HPLC in about 1 hour for the consumption of starting material. Analysis indicated disappearance of Santoflex 6PPD and the formation of the corresponding quinone-diimine in 97 area % by HPLC. A variety of isolation techniques can be used to isolate the product. A similar procedure as described in example 1 was used to isolate the product in almost quantitative yields.

EXAMPLE 3

A mixture of N-1,3-dimethylbutyl-N'-phenyl-p-phenylenediamine (Santoflex® 6PPD, 60 g., 0.224 moles) and hexanes (200 mL) was stirred and heated to 45° C. To this mixture was then added sodium hypochlorite (166 g., conc.=approx. 10.3%, 0.23 moles). The mixture was maintained at 45° C. and reaction was monitored by HPLC for the disappearance of Santoflex® 6PPD. The results are summarized in the following table:

| Sample # | Time, hrs. | Area % 6 QDI | Area % 6 PPD |
| --- | --- | --- | --- |
| 1 | 1 | 20.1 | 77.7 |
| 2 | 2 | 23.5 | 74.3 |
| 3 | 3 | 33.1 | 63.9 |
| 4 | 4.2 | 39.4 | 57.5 |
| 5 | 6 | 43.2 | 54.2 |
| 6 | 7 | 45.1 | 52.5 |
| 7 | 11 | 74.3 | 23.3 |
| 8 | 14 | 75.8 | 21.6 |
| 9 | 32 | 91.1 | 7.3 |
| 10 | 39 | 93.4 | 5.4 |

Analysis indicated disappearance of Santoflex® 6PPD and the formation of the corresponding quinonediimine. A variety of isolation techniques can be used to isolate the product. The technqiue used in the present example consisted of layer separation, washing of organic layer with water and the concentration of the hydrocarbon layer to deliver dark colored liquid. The liquid was identified to be the corresponding N-1,3-dimethylbutyl-N'-phenyl-quinonediimine (6QDI) which was isolated in almost quantitative yields.

In a similar reaction to that set forth above, effective mixing/stirring of the reaction resulted in complete conversion of 6PPD to 6QDI (100%) in less than five hours. This demonstrates that the rate of reaction can be increased significantly by increasing the mixing of the ingredients.

Additionally, the use of a higher strength (concentration) of sodium hypochlorite in the process of Example 3 results in an increased reaction rate compared to use of a lower concentration of sodium hypochlorite. Thus, increasing the concentration of sodium hypochlorite can significantly increase the rate of reaction of the claimed process.

EXAMPLE 4

The same procedure as described in example 3 was employed in the present example with an exception that a phase transfer catalyst was used in addition to all the other reagents. The catalyst used was tetrabutylammonium bromide. A mixture of N-1,3-dimethylbutyl-N'-phenyl-p-phenylenediamine (Santoflex® 6PPD, 60 g., 0.225 moles), hexanes (200 mL) and tetrabutylammonium bromide (1.2 g, 0.0037 moles) was stirred and heated to 45° C. To this mixture was then added sodium hypochlorite (166 g., conc.= approx 10.3%, 0.23 moles). The mixture was maintained at 45° C. and reaction was monitored by HPLC for the disappearance of Santoflex® 6PPD. The results are summarized in the following table:

| Sample # | Time, hrs. | Area % 6 QDI | Area % 6PPD |
| --- | --- | --- | --- |
| 1 | 0.5 | 90.1 | 8.8 |
| 2 | 1 | 96.1 | 1.6 |
| 3 | 1.5 | 99 | 0.5 |

Analysis indicated disappearance of Santoflex® 6PPD and the formation of the corresponding quinonediimine. A variety of isolation techniques can be used to isolate the product. The technique used in the present example consisted of layer separation, washing of organic layer with water and the concentration of the hydrocarbon layer to deliver dark colored liquid. The liquid was identified to be the corresponding N-1,3-dimethylbutyl-N'-phenyl-quinonediimine (6QDI) which was isolated in almost quantitative yields.

EXAMPLE 5

To a 500 mL flask was added N-1,3-dimethylbutyl-N'-phenyl-p-phenylenediamine (Santoflex® 6PPD, 100 g., 0.373 moles) which was immersed in a water bath maintained at 55° C. The reaction was sitrred and maintained at 55° C. while sodium hypochlorite (240 g., conc.=approx. 12.2%, 0.39 moles) was added over a period of 2.5 hrs. The mixture was maintained at 55° C. and the reaction was monitored by taking samples after the addition of sodium hypochlorite and analyzed by HPLC for the disappearnace of Santoflex® 6PPD. At the end of 3.25 hrs. the reaction had gone almost to completion to give the corresponding N-1, 3-dimethybutyl-N'-phenyl-quinonediimine (6QDI). A variety of isolation techniques can be used to isolate the product. The technique used in the present example consisted of addition of water, layer separation, and washing of organic layer with water to deliver dark colored liquid. The liquid was identified to be the corresponding N-1,3-dimethylbutyl-N'-phenyl-quinonediimine (6QDI) which was isolated in almost quantitative yields.

EXAMPLE 6

Following exactly same procedure of Example 5, the same quanitities of reagents as described in Example 5, and the same addition time were employed in the present example with an exception that a phase transfer catalyst was used in an addition to all the other reagents. The catalyst used was tetrabutylammonium bromide (2.0 g., 0.0062 moles). At the end of 1.5 hrs. the reaction had gone almost to completion to give the corresponding N-1,3-dimethylbutyl-N'-phenyl-quinonediimine (6QDI). A variety of isolation techniques can be used to isolate the product. The technique used in the present example consisted of addition of water, layer separation, and washing of organic layer with water to deliver dark colored liquid. The liquid was identified to be the corresponding N-1,3-dimethylbutyl-N'-phenyl-quinonediimine (6QDI) which was isolated in almost quantitative yields.

EXAMPLE 7

A mixture of Santoflex® 134 (5.0 g., which is a mixture of N-1,3-dimethylbutyl-N'-phenyl-p-phenylenediamine and N-1,4-dimethylpentyl-N'-phenyl-p-phenylenediamine) and acetonnitrile (50 mL) was stirred at room temperature. Sodium hypochlorite (12 g., conc.=approx. 12.5%) was then added to this mixture. The mixture was stirred at room temperature for 2 hours and then analyzed by HPLC for the consumption of the starting material. Analysis indicated disappearance of Santoflex® 134 and formation of the corresponding quinonediimine. A variety of isolation techniques can be used to isolate the product. The technique used in the present example consisted of concentration of the reaction mass to remove acetonitrile followed by treatment with a hydrocarbon (for example, toluene) and water, followed by layer separation and concentration of the hydrocarbon layer leading to a dark colored liquid. The product was identified to be the corresponding N-1,3-dimethylbutyl-N'-phenyl-quinonediimine (6QDI, 36 area %) and N-1,4-dimethylpentyl-N'-phenyl-quinonediimine (7QDI, 62 area %) which was isolated in almost quantitative yields.

EXAMPLE 8

A mixture of N-1,3-dimethylbutyl-N'-phenyl-p-phenylenediamine (Santoflex® 6PPD, 5.0 g., 0.019 moles), acetonitrile (200 mL), sodium hydroxide (25 g., 50% NaOH solution) and water (250 g.) was stirred and cooled to 0 to 10° C. To this mixture was passed chlorine in a controlled fashion and in controlled amounts and the mixture was analyzed by HPLC. The results are summarized in the following table:

| Sample # | Area % 6QDI | Area % 6PPD |
|---|---|---|
| 1 | 0 | 97.2 |
| 2 | 13.1 | 87.0 |
| 3 | 27.1 | 70.4 |
| 4 | 39.3 | 57.7 |
| 5 | 44.4 | 50.2 |
| 6 | 50.1 | 46.4 |
| 7 | 58.4 | 31.6 |

The mixture was stirred and then analyzed by HPLC for the consumption of starting material. Analysis indicated disappearance of Santoflex® 6PPD and formation of the corresponding quinonediimine. It was demonstrated that by passing controlled amounts of chlorine to the solution containing sodium hydroxide and Santoflex® 6PPD, the corresponding quinonediimine could be made in high selectivity. As mentioned above, a variety of isolation techniques can be used to isolate the product.

In case of processes using sodium hypochlorite, a product consisting of various combinations of 6QDI and Santoflex® 6PPD can be made.

According to this process, a mixture containing as little as 1.0% QDI to 100% QDI and 99% 6PPD to 0% 6PPD can be made by adjusting the charge of sodium hypochlorite. This process allows you to design a desired composition by controlling the amounts of reactants.

The following example illustrates this point more clearly:

EXAMPLE 9

A mixture of N-1,3-dimethylbutyl-N'-phenyl-p-phenylenediamine (Santoflex® 6PPD, 10 g., 0.037 moles) and acetonitrile (200 mL) was stirred at room temperature. To this mixture was then added sodium hypochlorite in small increments and the mixture was analyzed by HPLC after 1.5 hours at room temperature for the consumption of starting material. The procedure was repeated until all the Santoflex® 6PPD was reacted. Analysis indicated disappearance of Santoflex® 6PPD and formation of the corresponding quinonediimine in high selectivity. The results of HPLC analysis are summarized in the following table:

| Sample # | Area % 6QDI | Area % 6PPD |
|---|---|---|
| 1 | 0 | 97.6 |
| 2 | 1.55 | 96 |
| 3 | 3.26 | 95.8 |
| 4 | 5 | 93.5 |
| 5 | 21.2 | 76.8 |
| 6 | 28.5 | 69.8 |
| 7 | 34.8 | 62.6 |
| 8 | 41.8 | 55.5 |
| 9 | 51.2 | 45.9 |
| 10 | 54.5 | 34.1 |
| 11 | 67.2 | 28.4 |
| 12 | 88.9 | 6.33 |
| 13 | 97.3 | 0 |

A variety of isolation techniques can be used to isolate the product. The technique used in this example consisted of concentration of the reaction mass to remove acetonitrile followed by treatment with a hydrocarbon (for example, toluene at 300 mL) and water, followed by layer separation and concentration of the hydrocarbon layer leading to a dark colored liquid. The product was identified to be the corresponding N-1,3-dimethylbutyl-N'-phenyl-quinonediimine (6QDI) and isolated in almost quantitative yields.

The following example shows the use of a polar solvent (t-butyl alcohol) in admixture with a non-polar solvent to increase the rate of reaction compared to use of the non-polar solvent alone as in Example 3.

EXAMPLE 10

A mixture of 1,3-dimethylbutyl-N'-phenyl-p-phenylenediamine (Santoflex® 6PPD, 25.0 g., 0.093 moles), 2-methyl-2-propanol (t-butylalcohol, 2.5 g., 0.034 moles) and heptanes (60.0 g.) was stirred and heated to 48° C. To this mixture, sodium hypochlorite (56.0 g. At 13.4%, 0.100 moles) was metered in over a 30 minute period. The temperature of the mixture was maintained between 48–52° C. The progress of the reaction was monitored by HPLC for the disappearance of Santoflex® 6PPD. The results are summarized in the table below.

| Sample # | Time (minutes) | Area % 6QDI | Area % 6PPD |
|----------|----------------|-------------|-------------|
| 1 | 60 | 76.1 | 23.9 |
| 2 | 70 | 83.1 | 16.9 |
| 3 | 120 | 98.4 | 1.6 |

Other phenylenediamines, including Santoflex® 77PD [R$_1$=R$_2$=1,4-dimethylpentyl, R$_3$=hydrogen], Santoflex® 14 [R$_1$=phenyl, R$_2$=1,4-dimethylpentyl, R$_3$=hydrogen], Santoflex® IPPD, [R$_1$=phenyl, R$_2$=isopropyl, R$_3$=hydrogen], Santoflex® 44PD [R$_1$=R$_2$=sec-butyl, R$_3$=hydrogen], 4-aminodiphenylamine [R$_1$=H, R$_2$=phenyl, R$_3$=hydrogen], N,N'-diphenyl-para-phenylenediamine [R$_1$=R$_2$=phenyl, R$_3$=hydrogen] and N-cyclohexyl-N'-phenyl-para-phenylenediamine [R$_1$=cyclohexyl, R$_2$=phenyl, R$_3$=hydrogen] have also been successfully prepared according to the process of the present invention.

As demonstrated in the examples provided above, the reaction has been shown to be carried out in miscible solvents such as acetonitrile or methanol, or in an immiscible solvent such as hexanes. The reaction is very clean and the QDI end product can be obtained in very high yields with high selectivity. Various methods for increasing reaction rates include increasing stirring, addition of polar solvents to the reaction, and addition of phase transfer catalysts to the reaction.

The quinonediimines prepared by the process of the present invention exhibit multiple activities in vulcanized elastomers. These activities include long term antioxidant activity, along with antiozonant capacity. In fact, the antioxidant capacity of these antidegradants persists even after the vulcanizate has been extracted with solvents. In addition, quinonediimines provide these benefits without the negative effect on scorch generally associated with para-phenylenediamine antidegradants common to the industry. Summary of the activities of these compounds in rubber can be found in the literature. (Cain, M. E. et al., *Rubber Industry*, 216–226, 1975).

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the invention, it is claimed:

1. A highly selective process for preparing a quinonediimine by reacting the correspoding phenylenediamine with an oxidizing agent of the formula M$^+$OCl$^-$ wherein M is selected from a metal or an organic group.

2. The process of claim 1 wherein the hypochlorite is sodium hypochlorite (NaOCl).

3. The process of claim 1 wherein the phenylenediamine is an ortho- or para-phenylenediamine of the following Formula I:

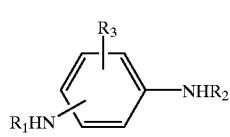

Formula I wherein R$_1$, R$_2$ and R$_3$ are the same or different and are selected from hydrogen, hydroxyl, halogen, alkyl, alkoxy, aryl, aralkyl, alkaryl, cycloalkyl, heterocycle, acyl, aroyl, carbamyl, carboxylic acids, esters, ethers, ketones, alcohols, thiols, alkylthiols, and cyano, and further wherein the resulting corresponding quinonediimine is of the following Formula IIa or IIb:

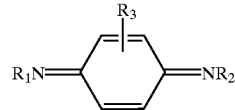

Formula IIa

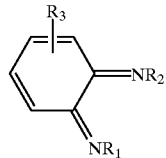

Formula IIb wherein R$_1$, R$_2$ and R$_3$ are the same as in the compound of Formula I.

4. The process of claim 3 wherein R$_1$=1,3-dimethylbutyl, R$_2$=phenyl and R$_3$=hydrogen.

5. The process of claim 3 wherein the compound of Formula I is N-1,3-dimethylbutyl-N'-phenyl-p-phenylenediamine.

6. The process of claim 3 wherein the phenylenediamine is a para-phenylenediamine and the resulting quinonediimine is a para-quinoediimine.

7. The process of claim 6 wherein R$_1$ and R$_2$=1,4-dimethylpentyl and R$_3$=hydrogen.

8. The process of claim 6 wherein R$_1$, R$_2$ and R$_3$ are selected from isopropyl, sec-butyl, cyclohexyl, phenyl, tolyl, 1,4-dimethylpentyl, naphthyl, 1-ethyl-3-methylpentyl, 1-methylheptyl, and hydrogen.

9. The process of claim 1 wherein the reaction takes place in the presence of a solvent.

10. The process of claim 9 wherein the solvent is selected from ketones, alcohols, nitriles, aliphatic and/or aromatic alkanes, aliphatic and/or aromatic alkenes, hydrocarbon solvents, water, and mixtures thereof.

11. The process of claim 9 wherein the solvent is selected from water, t-butyl alcohol, hexanes, acetonitrile, xylenes, heptanes, toluene, methanol, acetone, methyl isobutyl carbinol and methyl isobutyl ketone; each alone or in admixture.

12. The process of claim 9 wherein the solvent comprises a polar solvent and a non-polar solvent, further wherein the polar solvent increases the rate of reaction of the process.

13. The process of claim 1 wherein the reaction takes place in a neat system.

14. The process of claim 1 or 13 further comprising addition of a polar solvent in an amount which increases the rate of the reaction.

15. The process of claim 1 further comprising adding a phase transfer catalyst to the reaction to increase the reaction rate.

16. The process of claim 15 wherein the phase transfer catalyst is selected from quaternary ammonium salts, phosphonium salts, crown ethers, and polyethylene glycols.

17. The process of claim 15 wherein the phase transfer catalyst is tetra-N-butyl ammonium bromide.

18. The process of claim 1 wherein the reactants are mixed or stirred together, further wherein the reaction rate may be increased by increasing the mixing or stirring rate.

19. The process of claim 1 wherein the rate of reaction can be increased by increasing the strength (concentration) of the hypochlorite used.

20. A process for preparing a quinonediimine from a corresponding phenylenediamine wherein the phenylenediamine is an ortho- or para-phenylenediamine of the following Formula I:

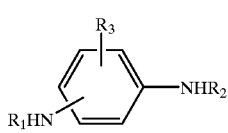

Formula I wherein $R_1$, $R_2$ and $R_3$ are the same or different and are selected from hydrogen, hydroxyl, halogen, alkyl, alkoxy, aryl, aralkyl, alkaryl, cycloalkyl, heterocycle, acyl, aroyl, carbamyl, carboxylic acids, esters, ethers, ketones, alcohols, thiols, alkylthiols, and cyano, and further wherein the resulting quinonediimine is of the following Formula IIa or IIb:

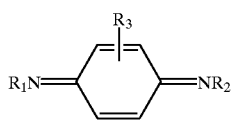

Formula IIa

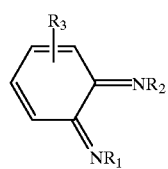

Formula IIb wherein $R_1$, $R_2$ and $R_3$ are the same as in the compound of Formula I; the reaction taking place by combining at least one compound of Formula I with sodium hypochlorite in the presence of a solvent system further wherein the reaction takes place at a temperature of from about $-200°$ C. to about $150°$ C.

21. The process according to claim 20 wherein water is further present in the solvent system.

22. The process according to claim 20 wherein the solvent system comprises a polar solvent and a non-polar solvent, further wherein the polar solvent increases the rate of reaction of the process.

23. The processss of claim 20 wherein the sodium hypochlorite is present in an amount of from about 0.1 to 100 equivalents hypochlorite per equivalent of phenylenediamine.

24. The process of claim 23 wherein the sodium hypochlorite is present in an amount of from about 0.3 to 5 equivalents hypochlorite per equivalent of phenylenediamine.

25. The process of claim 20 wherein the solvent is selected from water, ketones, alcohols, nitriles, aliphatic and/or aromatic alkanes, aliphatic and/or aromatic alkenes, hydrocarbon solvents and mixtures thereof.

26. The process of claim 20 wherein the phenylenediamine is a para-phenylenediamine and the resulting quinonediimine is a para-quinonediimine.

27. The process of claim 26 wherein $R_1$=1,3-dimethylbutyl, $R_2$=phenyl, and $R_3$=hydrogen.

28. The process of claim 26 wherein $R_1$ and $R_2$=1,4 dimethylpentyl and $R_3$=hydrogen.

29. The process of claim 26 wherein $R_1$, $R_2$ and $R_3$ are selected from isopropyl, sec-butyl, cyclohexyl, phenyl, tolyl, 1,4-dimethylpentyl, naphthyl, 1-ethyl-3-methylpentyl, 1-methylheptyl, and hydrogen.

30. The process according to claim 20 wherein the phenylenediamine component is comprised of a mixture of two or more phenylenediamines.

31. The process according to claim 20 wherein the reaction temperature is in the range of from about $0°$ C. to about $100°$ C.

* * * * *